(12) United States Patent
Tanaka et al.

(10) Patent No.: US 8,168,151 B2
(45) Date of Patent: May 1, 2012

(54) ORGANIC/INORGANIC COMPOSITE BIOMATERIALS AND PROCESS FOR PRODUCING THE SAME

(75) Inventors: Junzo Tanaka, Ibaraki (JP); Masanori Kikuchi, Ibaraki (JP); Noriichi Ito, Osaka (JP); Yoshinobu Mandai, Osaka (JP)

(73) Assignee: Japan Science and Technology Agency, Kawaguchi-shi (JP)

( * ) Notice: Subject to any disclaimer, the term of this patent is extended or adjusted under 35 U.S.C. 154(b) by 1336 days.

(21) Appl. No.: 10/492,937

(22) PCT Filed: Sep. 19, 2002

(86) PCT No.: PCT/JP02/09592
§ 371 (c)(1),
(2), (4) Date: Nov. 2, 2004

(87) PCT Pub. No.: WO03/035127
PCT Pub. Date: May 1, 2003

(65) Prior Publication Data
US 2005/0053638 A1    Mar. 10, 2005

(30) Foreign Application Priority Data

Oct. 19, 2001 (JP) .................................. 2001-322255
Mar. 11, 2002 (JP) .................................... 2002-65778

(51) Int. Cl.
| | | |
|---|---|---|
| *C01B 15/16* | (2006.01) | |
| *C01B 25/26* | (2006.01) | |
| *B05D 3/00* | (2006.01) | |
| *A61L 27/32* | (2006.01) | |
| *A61K 6/033* | (2006.01) | |

(52) U.S. Cl. ........ 423/308; 427/2.27; 623/919; 530/356
(58) Field of Classification Search .................... 514/183
See application file for complete search history.

(56) References Cited

U.S. PATENT DOCUMENTS

| | | | |
|---|---|---|---|
| 5,227,147 A | 7/1993 | Yoshimura et al. | |
| 5,231,169 A | 7/1993 | Constantz et al. | |
| 5,514,210 A | 5/1996 | Hirota et al. | |
| 5,532,217 A | 7/1996 | Silver et al. | |
| 5,607,590 A * | 3/1997 | Shimizu ....................... 210/490 |
| 5,739,286 A | 4/1998 | Silver et al. | |
| 6,311,690 B1 * | 11/2001 | Jefferies ....................... 128/898 |
| 6,384,197 B1 | 5/2002 | Weis et al. | |
| 6,395,036 B1 * | 5/2002 | Czernuszka et al. ........ 623/23.51 |

FOREIGN PATENT DOCUMENTS

| | | |
|---|---|---|
| EP | 0 945 146 A | 9/1999 |
| JP | 64-34372 | 2/1989 |
| JP | 10-127753 | 5/1998 |
| JP | 11-199209 | 7/1999 |
| WO | WO 93/12736 A | 7/1993 |

OTHER PUBLICATIONS

Weiner et al., 1986, FEBS Letters, vol. 206, No. 2, pp. 262-266.*
Machine translation of JP-11-199209: Tanaka et al., 1999, JP11-199209, pp. 1-7.*
Kikuchi M et al: "Self-organization mechanism in a bone-like hydroxyapatite/collagen nanocomposite synthesized in vitro and its biological reaction in vivo" Biomaterials, Elsevier Science Publishers BV., Barking, GB, vol. 22, No. 13, Jul. 1, 2001, pp. 1705-1711.
Masanori Kikuchi et al.; Materials Research Society Symposium Proceedings, vol. 599, pp. 51-53. 2000.
Masanori Kikuchi et al.; Bioceramics, vol. 12, pp. 393-396. 1999.
Masanori Kikuchi et al.; "Changes in Characters by Cross-Linking of Hydroxyapatite/Collagen Self-Organized Composites and Their Bone Tissue Reaction", The 20$^{th}$ Orthopaedic Ceramic Implant Meeting on Dec. 2, 2000, Programs and Abstracts.
International Search Report corresponding to Application No. EP 02 76 5594 dated Jun. 4, 2008.

* cited by examiner

*Primary Examiner* — Jeffrey S. Lundgren
*Assistant Examiner* — Meghan Finn
(74) *Attorney, Agent, or Firm* — Westerman, Hattori, Daniels & Adrian, LLP

(57) ABSTRACT

This invention provides organic/inorganic composite biomaterials constituted by composites of hydroxyapatite and collagen and having an average fiber length of 60 μm or longer, and a process for producing the same in which the calcium ion and phosphate ion concentrations in the reaction vessel are optimized through regulation of the concentration of a starting material and the flow rate. The organic/inorganic composite biomaterials have mechanical strength and a biodegradation rate suitable for artificial bones through the introduction of crosslinking therein.

19 Claims, 5 Drawing Sheets
(2 of 5 Drawing Sheet(s) Filed in Color)

A

B

C

ORGANIC/INORGANIC COMPOSITE BIOMATERIALS AND PROCESS FOR PRODUCING THE SAME

TECHNICAL FIELD

The present invention relates to organic/inorganic composite biomaterials comprising collagen and hydroxyapatite and a process for producing the same. More particularly, the present invention relates to organic/inorganic composite biomaterials having an average fiber length of 60 μm or longer and an excellent capacity for self-organization, organic/inorganic composite biomaterials having improved biodegradability through the introduction of crosslinking therein, and a process for producing the same.

BACKGROUND ART

At present, iliac bones, fibula bones, and the like of a patient are often used for regenerating bone defects. Use of a patient's own bones, however, imposes a heavy burden on a patient, and the amounts thereof that can be obtained are limited. Accordingly, it is necessary to supplement bone defects with artificial bones or artificial fillers. Properties required for such artificial biomaterials are mechanical properties such as strength and elasticity similar to those of natural bones and biological properties such as bioadaptability and bone conductivity.

Bones of vertebrates are originally composed of an inorganic substance (hydroxyapatite (HAp)) and an organic substance (collagen (Col)). They forms a specific nanocomposite structure in natural bones characterized in that the c-axis of hydroxyapatite is oriented along collagen fibers (self-organization), and this structure imparts bone-specific mechanical properties. Specifically, a simple combination of HAp and collagen cannot provide structures or properties similar to those of natural bones.

In addition to biocompatibility, it is necessary for such artificial biomaterials to have effects of actively accelerating bone regeneration by being fused with bone tissues. Specifically, artificial materials need to have bone conductivity or bioactivity so that the materials can being gradually resorbed after implantation in the body, and involved in the bone regeneration cycle, thereby substituting the patient's own bone. An inorganic substance (HAp) has excellent bone-compatibility, and an organic substance (collagen) is capable of accelerating cell adhesion and cell differentiation. Accordingly, composites of these two substances are expected to have excellent properties as artificial biomaterials.

A variety of studies have been made to develop organic/inorganic composite biomaterials that are more similar to natural bones by using hydroxyapatite and collagen. For example, JP Patent Publication (Kokai) No. 7-101708 A (1995) discloses a process for producing an apatite-organic substance composite in which a molded body having the Young's modulus similar to that of natural bones is obtained with the gradual addition of a mixed solution of collagen and phosphoric acid in a suspension of calcium hydroxide. JP Patent Publication (Kokai) No. 11-199209 A (1999) discloses a process for producing organic/inorganic oriented composite materials, wherein an aqueous phosphoric acid solution containing collagen and an aqueous calcium salt solution are simultaneously added dropwise to a reaction vessel while regulating pH and temperature at the time of reaction, and a resulting sediment is pressed, thereby obtaining materials similar to natural bones. Further, JP Patent Publication (Kokai) No. 2000-5298 A discloses a technique for accelerating the formation of apatite on a collagen surface with the use of organic acid.

Fiber lengths of composites obtained by such conventional techniques were, however, approximately between several μm and 20 μm, which was not yet sufficient to realize self-organization.

DISCLOSURE OF THE INVENTION

The objects of the present invention are to discover optimal conditions for accelerating self-organization of the aforementioned composites of collagen and hydroxyapatite and to provide organic/inorganic composite biomaterials having mechanical strength and biodegradability that are suitable for artificial bones.

The present inventors have conducted concentrated studies in order to attain the above objects, and they have considered that composites having an excellent capacity for self-organization could be obtained if the biomimetic microenvironment at the time of osteogenesis could be reproduced with higher consistency. Thus, they have set a variety of conditions. As a result, they have found that composites having unprecedentedly long fibers can be obtained by optimizing the concentrations of collagen, calcium salt, and phosphate in the reaction vessel through regulation of the starting concentrations and the flow rates thereof. Further, they have found that biodegradability of the composites can be controlled by introducing crosslinking into collagen. This has led to the completion of the present invention.

More specifically, the present invention provides the following (1) to (14).

(1) Organic/inorganic composite biomaterials constituted by composites comprising hydroxyapatite and collagen with an average fiber length of 60 μm or longer.

(2) The organic/inorganic composite biomaterials according to (1), wherein the composites have microporous structures in which the c-axis of hydroxyapatite is oriented along collagen fibers.

(3) The organic/inorganic composite biomaterials according to (1) or (2), wherein the collagen is an enzyme-solubilized collagen.

(4) A process for producing the organic/inorganic composite biomaterials according to any one of (1) to (3), which comprises:
simultaneously adding dropwise to a reaction vessel an aqueous calcium salt solution and an aqueous phosphate solution containing collagen to maintain the calcium ion concentration at 3.75 mM or lower and the phosphate ion concentration at 2.25 mM or lower in the reaction vessel, and pressing the resulting composite.

(5) The process according to (4), wherein the ratio of the weight of hydroxyapatite to that of collagen generated in the reaction vessel is between 3:2 and 9:1.

(6) The process according to (4) or (5), wherein the calcium ion concentration and the phosphate ion concentration in the reaction vessel are maintained by regulating the following 1) and/or 2):
1) the flow rates of an aqueous calcium salt solution and an aqueous phosphate solution containing collagen to a reaction vessel; and
2) the starting concentration of an aqueous calcium salt solution and that of an aqueous phosphate solution containing collagen.

(7) The process according to (6), wherein the average flow rate of an aqueous calcium salt solution is 5 to 25 ml/min, the starting concentration of an aqueous calcium salt solution is 400 mM or lower, and the starting concentration of an aqueous phosphate solution is 120 mM or lower when the ratio of the weight of hydroxyapatite to that of collagen generated is maintained between 70:30 and 85:15.

(8) The process according to any one of (4) to (7), wherein the pH level of the reaction solution in the reaction vessel is maintained between 7 and 11.

(9) The process according to (8), wherein the temperature of the reaction solution is maintained between 35° C. and 40° C.

(10) The process according to any one of (4) to (9), further comprising introducing crosslinking of collagen in the organic/inorganic composite biomaterials obtained by the aforementioned process.

(11) The process according to (10), wherein the crosslinking is introduced by a reaction utilizing glutaraldehyde.

(12) The process according to (11), wherein 10 μmol to 10 mmol of the glutaraldehyde is used per g of collagen in organic/inorganic composite biomaterials.

(13) The organic/inorganic composite biomaterials according to any one of (1) to (3), wherein collagen is crosslinked.

(14) The organic/inorganic composite biomaterials according to any one of (1) to (3) and (13), which are formed into sheets, sponges, or porous bodies.

The present invention is hereafter described in detail.

1. The Organic/Inorganic Composite Biomaterials of the Present Invention

The organic/inorganic composite biomaterials of the present invention are constituted by "composites comprising collagen and hydroxyapatite" having an average fiber length of 60 μm or longer and enhanced strength resulting from their long fiber lengths. The term "average fiber length" refers to the average length of fibers constituting the aforementioned composites, and this average length can be measured visually or using specific instrument (e.g., Rapid-Vue, manufactured by Beckman-Colter). The aforementioned average fiber length is more preferably 1 mm or longer, and further preferably 3 mm or longer.

In the organic/inorganic composite biomaterials of the present invention, hydroxyapatite and collagen are preferably oriented in a self-organized manner to form composites similar to natural bones. The term "self-organized" generally refers to the "formation of a specific structure characterized by an assembly of homologous or heterologous atoms, molecules, fine particles, or the like through non-covalent interaction" (Seikagaku Jiten (Dictionary of Biochemistry), Tokyo Kagaku Dozin Co., Ltd.). In the present invention, this term particularly refers to a microporous structure characterized by the same orientation of calcium phosphate having an apatite structure (hydroxyapatite (HAp)) as natural bones, in which the c-axis of HAp is oriented along collagen fibers.

Hydroxyapatite is generally denoted by the chemical formula $Ca_5(PO_4)_3OH$, however, it includes a group of compounds referred to as calcium phosphate, such as $CaHPO_4$, $Ca_3(PO_4)_2$, $Ca_4O(PO_4)_2$, $Ca_{10}(PO_4)_6(OH)_2$, $CaP_4O_{11}$, $Ca(PO_3)_2$, $Ca_2P_2O_7$, or $Ca(H_2PO_4)_2 \cdot H_2O$ as evidenced by the nonstoichiometric properties of its reaction. Also, hydroxyapatite is basically composed of a compound represented by the formula $Ca_5(PO_4)_3OH$ or $Ca_{10}(PO_4)_6(OH)_2$, and a part of the Ca component may be substituted with at least one member selected from Sr, Ba, Mg, Fe, Al, Y, La, Na, K, H, and the like. A part of the ($PO_4$) component may be substituted with at least one member selected from $VO_4$, $BO_3$, $SO_4$, $CO_3$, $SiO_4$, and the like. A part of the (OH) component may be substituted with at least one member selected from F, Cl, O, $CO_3$, and the like. Some of these components may be deficient. In general, some of the apatite $PO_4$ and OH components in natural bones are substituted with $CO_3$. Accordingly, inclusion of $CO_3$ from the atmosphere and partial substitution with each component (about 0% to 10% by mass) may occur during the production of the composite materials of the present invention.

Hydroxyapatite is generally microcrystalline, noncrystalline, or crystalline. Alternatively, it may exist in the form of an isomorphic solid solution, substitutional solid solution, or interstitial solid solution. It may comprise a nonstoichiometric deficiency. The atomic ratio of calcium/phosphorus (Ca/P) in this hydroxyapatite is preferably in the range between 1.3 and 1.8. In particular, the range between 1.5 and 1.7 is more preferable. When the atomic ratio is in the range between 1.3 and 1.8, the composition and the crystal structure of apatite in the product (a calcium phosphate compound) can be similar to those in bones of vertebrates. This improves biocompatibility and bioabsorbability.

At present, about 20 different collagen molecular species are known to be present in a wide variety of animal tissues ranging from mammalians to fish. These are generically denoted as "collagens." The species, the location of tissue, the age, and other factors regarding the animal that is a starting material for the collagen used in the present invention are not particularly limited, and any type of collagen can be used. In general, collagens obtained from skin, bones, cartilage, tendons, organs, or the like of mammalians (such as cow, pig, horse, rabbit, or mouse) and birds (such as chicken) are used. Also, collagen-like proteins obtained from skin, bones, cartilage, fins, scales, organs, or the like of fish (such as cod, left-eyed flounder, right-eyed flounder, salmon, trout, tuna, mackerel, sea bream, sardine, or shark) may be used as starting materials. Alternatively, collagen may be obtained by gene recombination techniques instead of by extraction from animal tissues.

Among the molecular species of collagens, the quantity of type I collagens is the largest, and they have been well studied. In general, when simple reference is made to a "collagen," it often indicates a type I collagen. The molecular species of the collagen used in the present invention is not particularly limited, and a type I collagen is preferably a main component. Collagen may be prepared by adequately subjecting an amino acid residue of the collagen protein to chemical modification such as acetylation, succination, maleylation, phthalation, benzoylation, esterification, amidation, or guanidination.

Collagen may be prepared by extraction from the aforementioned starting material (excluding the gene recombination technique) by a neutral buffer or dilute acid such as hydrochloric acid, acetic acid, or citric acid. Collagen extracted by the neutral buffer is referred to as neutral salt-soluble collagen, and that extracted by the dilute acid is referred to as acid-soluble collagen. However, the amount of collagen extracted is small in both cases, and a majority thereof remains as insoluble collagen. Enzyme solubilization method and alkali solubilization method are known as methods for solubilizing this insoluble collagen. Collagen obtained by the enzyme solubilization method is referred to as enzyme-solubilized collagen, and that obtained by the alkali solubilization method is referred to as alkali-solubilized collagen. Both can be solubilized as molecular collagens with yields of substantially 100%.

The method for preparing collagen used in the present invention (extraction type) is not particularly limited. If the molecular weight of solubilized collagen is large, however, the strength of a composite becomes insufficient because of steric hindrance. Accordingly, the use of monomeric (monomolecular) collagen is preferable. In enzyme-solubilized collagen and alkali-solubilized collagen, the monomeric collagen content is high, and non-helical regions (telopeptides) having a majority of collagen antigenicity are selectively degraded and removed during the step of production. Thus, they are particularly adequate for the organic/inorganic composite biomaterials of the present invention. If these non-helical regions are degraded and removed from collagen, the resulting form of collagen is referred to as "atelocollagen."

The isoionic point of enzyme-solubilized collagen is different from that of alkali-solubilized collagen. The isoionic point is the pH level where both positive and negative charges, which are derived from a dissociable group inherent to a protein molecule, repel each other. In the case of collagen, when the pH level approaches the region of the isoionic point, solubilized collagen is known to become fibrous. In general, the isoionic point of the enzyme-solubilized collagen is between pH 8 and 9, and that of the alkali-solubilized collagen is between pH 4 and 5. In the present invention, it is preferable to use the enzyme-solubilized collagen in a reaction vessel maintained at conditions between pH 7 and 11, where the fiberization and self-organization of collagen are likely to occur. Examples of enzymes for solubilization include pepsin, trypsin, chymotrypsin, papain, and pronase. Pepsin and pronase are preferably used from the viewpoint of easy handleability after the enzyme reaction.

2. A Process for Producing Organic/Inorganic Composite Biomaterials

The organic/inorganic composite biomaterials of the present invention are produced from at least three components, i.e., collagen, phosphate, and calcium salt. In the present invention, the phosphate includes phosphoric acid, and the calcium salt includes calcium hydroxide, although they are not technically defined as "salts."

Examples of phosphagens for an aqueous phosphate solution used in the present invention include disodium hydrogenphosphate, sodium dihydrogen phosphate, dipotassium hydrogen phosphate, potassium dihydrogen phosphate, and phosphoric acid. The aqueous phosphate solution dissolves the collagen, and it is subjected to reactions.

Examples of calcium sources for an aqueous calcium salt solution used in the present invention include calcium carbonate, calcium acetate, and calcium hydroxide. This aqueous calcium salt solution may be a suspension as long as it is homogenous. For example, calcium carbonate is burned and then pulverized using a mortar or the like to prepare calcium hydroxide, and water is added thereto to obtain a suspension of calcium hydroxide. The thus obtained suspension can be preferably used.

In the process for producing the organic/inorganic composite biomaterials of the present invention, the aqueous calcium salt solution and the aqueous phosphate solution containing collagen are simultaneously added dropwise to the reaction vessel. The term "simultaneous" is not limited to dropwise addition at the precisely same time. It also includes the form of dropwise addition in which a small amount (approximately 0.01 to 5 ml) of each of these solutions is separately added in alternate shifts. These solutions may be continually or intermittently added as long as they are simultaneously added.

An adequate amount of pure water is previously placed in the reaction vessel. The amount of pure water is not particularly limited. Preferably, it is substantially the same as the amount of the aqueous calcium salt solution to be used.

In the process for production of the present invention, it is important to maintain the calcium ion concentration at 3.75 mM or lower and the phosphate ion concentration at 2.25 mM or lower in the reaction vessel. This is because the preferable self-organization of the composite is impeded if the calcium ion or phosphate ion concentration exceeds the upper limit of the aforementioned range. This impedance is considered to be caused by spontaneous nucleus formation that occurs when the concentrations of ions convected in the reaction vessel exceed the concentrations thereof in body fluids. More preferably, the calcium ion concentration is maintained at 2.5 mM or lower, and the phosphate ion concentration is maintained at 1.5 mM or lower, so that a composite having an average fiber length of 1 mm or longer can be obtained.

In the process for production of the present invention, the ratio of the weight of hydroxyapatite to that of collagen generated in the reaction vessel is preferably between 3:2 and 9:1, and more preferably between 70:30 and 85:15. Specifically, it is important for self-organization that the ratio of the weight of hydroxyapatite to that of collagen when an ideal reaction takes place be similar to the ratio in the composition of natural bone (75:25).

In the process for production of the present invention, the calcium ion and phosphate ion concentrations in the reaction vessel can be maintained in the desired range by controlling: 1) the flow rates of an aqueous calcium salt solution and an aqueous phosphate solution containing collagen to a reaction vessel; and/or 2) the starting concentration of an aqueous calcium salt solution and that of an aqueous phosphate solution containing collagen.

The term "starting concentration" used herein refers to the concentration of each component (e.g., an aqueous calcium salt solution and an aqueous phosphate solution containing collagen) that has been independently prepared before being placed in the reaction vessel. The term "flow rate" refers to the amount of each reaction solution to be transferred to the reaction vessel per unit time. The flow rate can be easily controlled using a commercialized tube pump or other means.

The flow rate of the aqueous calcium salt solution and that of the aqueous phosphate solution are adjusted in such a manner that dropwise addition of both solutions is completed at substantially the same time (within 10 minutes at longest).

In a preferable embodiment of the present invention, the starting concentration of the aqueous calcium salt solution is 400 mM or lower, and preferably 50 to 200 mM when the average flow rate of the aqueous calcium salt solution is set between 5 and 25 mM/min, in order to maintain the ratio of the weight of hydroxyapatite to that of collagen generated between 70:30 and 85:15. The concentration of an aqueous phosphoric acid solution containing collagen is 120 mM or lower, and preferably between 15 and 96 mM. The term "average flow rate" refers to the average amount of a solution to be transferred to the reaction vessel per minute in consideration of, for example, the on-off control of the pump.

The ratio of the amount of an aqueous phosphoric acid solution containing collagen to that of an aqueous calcium salt solution is preferably between 3:1 and 1:3. When a small amount of an aqueous phosphoric acid solution containing collagen is used, the resulting material disadvantageously comprises an excess amount of calcium, which results in reduced strength. In contrast, a small amount of an aqueous calcium salt solution causes calcium deprivation and lowers the Young's modulus, which sometimes results in reduced strength (Japanese Patent Publication (Kokai) No. 11-199209 A (1999)).

In the present invention, the pH level of the reaction solution is preferably between 7 and 11, and the reaction solution is preferably added dropwise so as to keep the pH variation within 1. More preferably, the pH level is between 7 and 9, and the pH variation is within 0.5. Native collagen causes sedimentation at the isoelectric point when the pH is between 7 and 11 to regenerate fibers, and calcium phosphate is likely to cause sedimentation in this pH range. Thus, self-organization of calcium phosphate and collagen is promoted in this pH range. When the pH level exceeds 11, however, water molecules are hydrated around collagen molecules, and it becomes difficult for water molecules to dissociate in the later step of pressing. This could increase the water content, block the self-organization, and decrease the strength of the composite. In contrast, both calcium phosphate and collagen become less likely to sediment if the pH level is below 7. When the pH variation exceeds 1, nucleus formation of calcium phosphate on collagen is inhibited, and thereby self-organization is inhibited (Kikuchi et al., Biomaterials 22, 2000, pp. 1705-1711).

In the process for production of the present invention, an adequate pH level is easily maintained with the use of a pH controller. A pH controller comprises a means for measuring pH of the reaction solution and a means for controlling the amounts of both solutions to be added. This pH controller regulates the amounts of both solutions to be added based on the pH levels of the both solutions so as to maintain a certain level (e.g., ±0.3) relative to the pH level that was set as an expected value (e.g., 10). An example of a pH controller is that manufactured by Nissin. Reaction is preferably carried out while constantly stirring the both aqueous solutions and the reaction solution in order to maintain the uniform pH level of the reaction solution.

In the process for production of the present invention, the temperature of the reaction solution is preferably maintained between 35° C. and 40° C. In this temperature range, composites can be formed under conditions similar to those in bodies.

The sediment generated from the reaction solution is subjected to filtration and dehydration, followed by pressing. Thus, the organic/inorganic composite biomaterials of the present invention characterized by a self-organization, in which microcrystalline calcium phosphate is oriented and coupled with collagen macromolecules, can be obtained.

Pressing is preferably carried out in a temperature range between 0° C. and 110° C. and in a pressure range between 10 MPa and 5 GPa. When pressing is carried out in this temperature range, most of water contained in the sediment is rapidly removed. Temperature is preferably between 25° C. and 60° C. where a large amount of water is discharged, with the range between 35° C. and 45° C. being particularly preferable.

It is preferable to conduct pressing with ultrasonication since self-organization can be further promoted by this procedure. An example of an apparatus for applying pressure that can be used for pressing in the present invention is the CIP, manufactured by Kobe Steel, Ltd.

3. Configurations and Forms of Organic/Inorganic Composite Biomaterials

The configurations and forms of the organic/inorganic composite biomaterials of the present invention are not particularly limited. Biomaterials can take any desired configuration and form in accordance with the applications thereof. For example, they can be blocks, pastes, films, or particles. The organic/inorganic composite biomaterials of the present invention have unprecedentedly long fibers, and thus, particularly suitable forms thereof are sheets, porous bodies, or sponges in which fibers are interwined with each other. The term "sheet" refers to a form such as thin paper, the term "porous body" refers to a constitution in which indefinite number of pores (gaps) exist, and the term "sponge" refers to a constitution in which flexible microporous bodies (an indefinite number of approximately several-µm to several-10-µm pores (gaps)) exist. Pressing into sheets may be carried out by flattening the sediment after reaction by a conventional technique. Porous bodies and sponges may be prepared by lyophilization of the synthesized composite fibers after removing water by filtration or centrifugation.

The organic/inorganic composite biomaterials of the present invention become as elastic as sponges upon moisture absorption and have excellent bioadaptability, bone inductivity, or bone conductivity. When the composite biomaterials are used as implants, therefore, they may be once immersed in adequate liquid such as physiological saline before use. The implanted composite biomaterials can be rapidly fused with bone tissues and integrated into the hard tissues of the recipient.

4. Regulation of Biodegradability by Crosslinking Organic/Inorganic Composite Biomaterials Crosslinking of collagen can be introduced in the thus obtained organic/inorganic composite biomaterials to regulate the rate of biodegradation. Preferably, crosslinking is directly introduced without isolating the composite from a reaction solution. A minor amount of collagen or polysaccharides (1 to 100 mol % relative to the amount of collagen in the composite) may be added in order to increase the points of crosslinking.

Any method, such as chemical crosslinking using a crosslinking agent or condensing agent or physical crosslinking using γ rays, ultraviolet rays, thermal dehydration, an electron beam, or the like, may be employed. Examples of crosslinking agents that can be used include: aldehyde crosslinking agents such as glutaraldehyde or formaldehyde; isocyanate crosslinking agents such as hexamethylene diisocyanate; carbodiimide crosslinking agents such as 1-ethyl-3-(3-dimethylaminopropyl) carbodiimide hydrochloride; polyepoxy crosslinking agents such as ethylene glycol diethyl ether; and transglutaminase. The amount of a crosslinking agent used is preferably between about 10 µmol and 10 mmol per g of collagen.

Crosslinking as mentioned above may involve any portions of collagens. Particularly preferable crosslinking occurs between a carboxyl group and a hydroxyl group, between a carboxyl group and a ϵ-amino group, or between ϵ-amino groups. Crosslinking is preferably introduced in at least 1%, and more preferably at least 5%, of reactive functional groups. If crosslinking is insufficient, biodegradation takes place rapidly. Thus, sufficient effects of supplementing bone defects cannot be expected. Attention should be given to the use of a crosslinking agent since the excessive use of a crosslinking agent disadvantageously increases the water content in the composite after the introduction of crosslinking between fibers constituting a composite and inhibits particle-particle bonds to decrease the strength of the composite.

Among the aforementioned methods for crosslinking, chemical crosslinking using a crosslinking agent such as glutaraldehyde is particularly preferable from the viewpoints of controllability of the amount of crosslinking and bioadaptability of the resulting composite. A method for crosslinking using glutaraldehyde is hereafter described as a preferable embodiment of the present invention.

The reaction solution of a composite of hydroxyapatite and collagen obtained in the section above is allowed to age immediately after or 3 hours after the synthesis of a composite. Thereafter, glutaraldehyde is added thereto while vigorously stirring, and the mixture is allowed to react for 10 minutes. After the crosslinking, a composite is immediately subjected to filtration and washed three times with pure water to remove excessive glutaraldehyde.

The amount of glutaraldehyde to be added is preferably 10 μmol to 10 mmol, and particularly preferably 10 μmol to 1 mmol, per g of collagen in the composite biomaterials. The temperature of reaction solution is preferably maintained between 0° C. and 40° C.

The resulting crosslinked composite biomaterials have enhanced mechanical strength and a slower rate of biodegradation than non-crosslinked composite biomaterials. Thus, the crosslinked composite biomaterials have the capacity for remaining in the body, which is required for artificial bones and the like. The rate of biodegradation can be evaluated by, for example, implanting the composite biomaterials into the bones of mice, rats, rabbits, or the like and then inspecting the capacity of the biomaterials for remaining in the body. Mechanical strength can be evaluated based on, for example, the three-point bending strength or the Young's modulus determined based thereon.

More specifically, the organic/inorganic composite biomaterials that had been crosslinked with 10 μmol to 10 mmol of glutaraldehyde per g of collagen had enhanced mechanical strength of 15 MPa or more after the crosslinking, as opposed to 7 MPa before the crosslinking. While non-crosslinked samples were substantially resorbed (90% or more thereof) within 4 weeks in natural bones, approximately 50% or more of the crosslinked composite biomaterials remained in natural bones even 4 weeks later.

5. Application of Organic/Inorganic Composite Biomaterials

The organic/inorganic composite biomaterials of the present invention may contain the essential components, i.e., calcium salt, phosphate, and collagen, as well as other components within the scope of the present invention. Examples of such components include inorganic salts such as St, Mg, and $CO_3$, organic substances such as citric acid and phospholipids, Bone Morphogenetic Proteins, and agents such as anti-cancer agents.

The organic/inorganic composite biomaterials obtained in the present invention have strength and compositions similar to those of natural bones. Also, the organic/inorganic composite biomaterials of the present invention have effects of sustaining drug release, bone inductivity, and bone conductivity due to the biosolubility of both constituents, i.e., collagen and calcium phosphate.

Bone marrow, liver, and other tissues can be reconstructed by conducting tissue culture using the organic/inorganic composite biomaterials of the present invention containing highly bioactive cytokines as a scaffold in a biomimetic environment to which dynamics or electricity had been applied or in vivo. For example, when the composite materials of the present invention impregnated with anti-cancer agents are used for reconstructing bones resected due to osteogenic sarcoma, carcinoma recurrence can be prevented and the generation of hard tissue in the patient can be induced.

Accordingly, the composite materials of the present invention can be utilized as, for example, materials for bone reconstruction capable of substituting natural bone due to the bone inductivity and bone conductivity, bioactive scaffold for tissue engineering comprising amino acids, saccharides, and cytokines, and biocompatible drug carriers for sustained release such as anti-cancer agents. Specific examples of applications include artificial bones, artificial joints, cements for tendons and bones, dental implants, percutaneous terminals for catheters, drug carriers for sustained release, chambers for bone marrow induction, and chambers or base materials for tissue reconstruction.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

This description includes part or all of the contents as disclosed in the descriptions of Japanese Patent Application Nos. 2001-322255 and 2002-65778, which are priority documents of the present application.

BEST MODES FOR CARRYING OUT THE INVENTION

The present invention is hereafter described in more detail with reference to the examples, although the technical scope of the present invention is not limited thereto.

Example 1

Examination of Starting Material Concentration

1. Testing Method

The flow rate of calcium hydroxide was fixed at 15 ml/min, and the concentrations and the amounts of starting materials, i.e., a calcium hydroxide suspension and an aqueous phosphoric acid solution, were varied as shown in Table 1. The flow rate of an aqueous phosphoric acid solution was adjusted so that dropwise addition of a calcium hydroxide suspension was completed at substantially the same time as that of an aqueous phosphoric acid solution. The amount of atelocollagen (extracted from porcine dermis, Nitta Gelatin Inc.) to be added to the aqueous phosphoric acid solution was constantly 2.01 g, and pure water in the same amount with the calcium hydroxide suspension had been previously placed in a reaction vessel. Under the aforementioned conditions, the ratio of the weight of hydroxyapatite (HAp) to that of collagen (Col) becomes 80:20 when an ideal reaction takes place.

Figure 1:
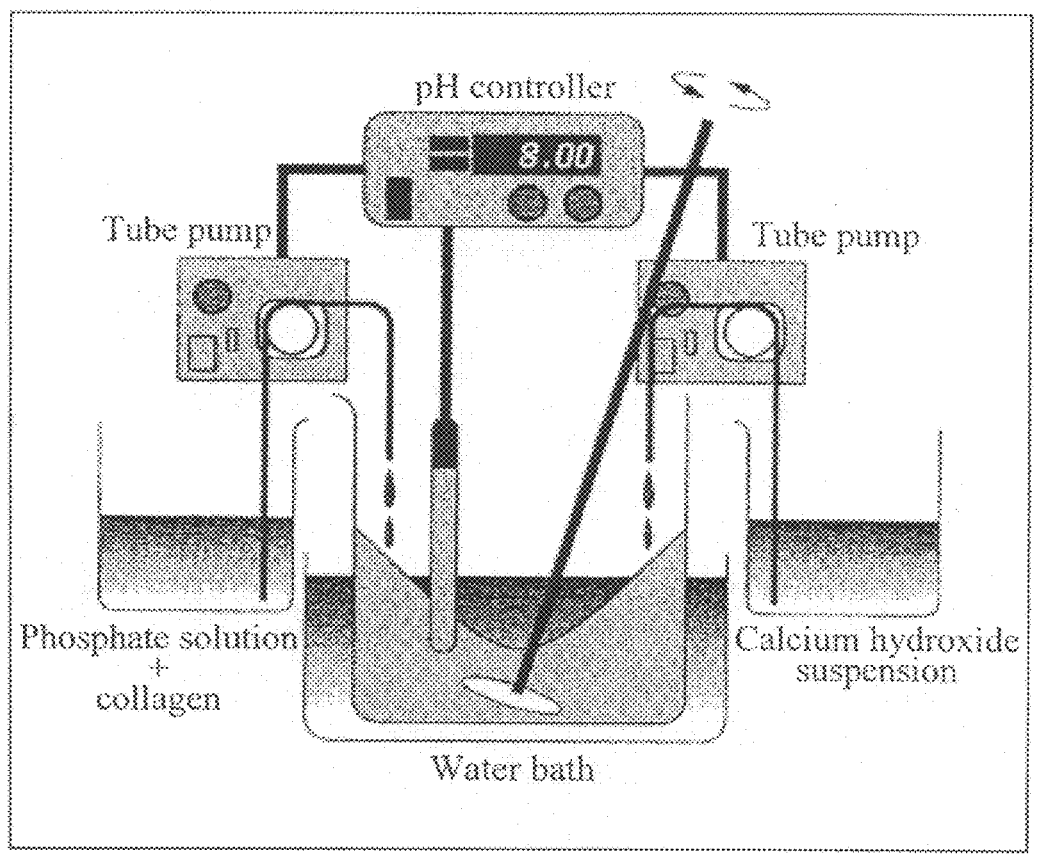
FIG. 1 shows an apparatus for experimentation used in Example 1 and Example 2 (an apparatus for simultaneous dropwise addition). The pH level is controlled by a pH controller and the temperature is regulated by a water bath in this apparatus.

The reaction was carried out at 40° C. at pH 9 (maintained at pH 9±0.3 using a pH controller, manufactured by Nissin) by simultaneously adding both solutions dropwise at a constant flow rate while vigorously stirring and controlling the on/off operation of the pump. The apparatus used in this test is shown in FIG. 1.

Other details of the test were in accordance with the method described in Kikuchi et al. (Biomaterials 22, 2000, pp. 1705-1711).

2. Evaluation of a Composite

The fiber length of the obtained composite was measured and the state of self-organization was verified. The composite was subjected to dehydration by uniaxial pressing at 25° C. at 20 MPa for 24 hours, and the resultant was subjected to a three-point bending test, thermal analysis, and a swelling test. Details of tests and the test results (Table 1) are given below.
1) Measurement of Fiber Lengths The resulting sediment was filtered, dehydrated, and then subjected to measurement of fiber length using the Rapid-Vue (Beckman-Colter). Fiber lengths exceeding the measurement limit of the apparatus were measured visually.

2) Three-Point Bending Test

The composite (20×5×3 mm³) after dehydration pressing was employed as a sample, and its three-point bending strength was assayed using AGS-1kN (Shimadzu Corporation) at a crosshead speed of 500 μm/min at a span of 15 mm. Assay was carried out five times, and the Young's modulus was determined based on the obtained load-distortion curve.

3) Thermal Analysis

The composite (10×5×3 mm³) after dehydration pressing was employed as a sample and subjected to measurement using RC-412 (LECO).

4) Swelling Test

The composite (5×5×5 mm³) after dehydration pressing was employed as a sample, immersed in 30 ml of PBS (Dainippon Pharmaceutical Co., Ltd.), and subjected to measurement of weight over a period of 1 to 21 days in order to determine the swelling ratio (the equation thereof shown below).

Swelling ratio(%)=[$(Wx-Wo)/Wo$]×100

(Wx: initial weight; Wo: weight after immersion)

3. Calculation of (Initial) Concentration in the Reaction Vessel

It was hypothesized that the calcium ion and phosphate ion concentrations in the reaction vessel at the initial stage of reaction would be substantially the same as the amounts of these ions to be supplied to the reaction vessel per minute, and these levels were determined by the equation shown below. The average flow rate was set at one-half of the flow rate of the pump in view of the on-off control of the pump. This approximate value was confirmed to be substantially consistent with the value obtained based on the total number of hours required for the reaction.

Concentration in the reaction vessel=(concentration of a starting material×average flow rate)/(amount of pure water in the reaction vessel)

(average flow rate: the set rate of the pump×½)

TABLE 1

Evaluation of properties of composites depending on level of starting material

| | | No. | | | | |
|---|---|---|---|---|---|---|
| | | 1 | 2 | 3 | 4 | 5 |
| Concentration of calcium hydroxide (mM) | | 50 | 100 | 160 | 200 | 400 |
| Amount of calcium hydroxide (ml) | | 1,600 | 800 | 500 | 400 | 200 |
| Concentration of an aqueous phosphoric acid solution (mM) | | 15 | 30 | 96 | 60 | 120 |
| Amount of an aqueous phosphoric acid solution (ml) | | 3,200 | 1,600 | 500 | 800 | 400 |
| Amount of pure water in a reaction vessel (ml) | | 1,600 | 800 | 500 | 400 | 200 |
| Ca concentration in a reaction vessel (mM) | | 0.234 | 0.938 | 2.4 | 3.75 | 15 |
| $PO_4$ concentration in a reaction vessel (mM) | | 0.141 | 0.563 | 1.44 | 2.25 | 9 |
| Fiber length - average | | 3–5 mm | 5–7 mm | 3–5 mm | 1–2 mm | 60 μm |
| Strength test | Strength (MPa) | 4.4 ± 0.4 | 11.6 ± 1.5 | 10.0 ± 0.5 | 7.0 ± 0.6 | 9.8 ± 0.3 |
| | Strength after dehydration (MPa) | 25.0 ± 2.0 | 50.0 ± 3.0 | 30 ± 2.0 | 21.0 ± 3.0 | 27.0 ± 2.0 |
| | Young's modulus (GPa) | 0.13 ± 0.03 | 0.66 ± 0.15 | 0.50 ± 0.12 | 0.25 ± 0.05 | 0.56 ± 0.05 |
| | Young's modulus after dehydration (GPa) | 1.80 ± 0.17 | 3.50 ± 1.00 | 2.80 ± 0.81 | 0.77 ± 0.05 | 1.80 ± 0.10 |
| Thermal analysis | Water content in the composite (%) | 55 | 37 | 35 | 34 | 23 |
| | Amount of HAp in the composite (%) | 34 | 49 | 51 | 52 | 62 |
| | Amount of Col in the composite (%) | 11 | 14 | 14 | 14 | 15 |
| | HAp/Col ratio after dehydration | 76/24 | 78/22 | 78/22 | 79/21 | 81/19 |
| Swelling test | Swelling ratio 1 week later (%) | 28.1 | 32.5 | 38.4 | 51.8 | 57.2 |

4. Results

Figure 2:
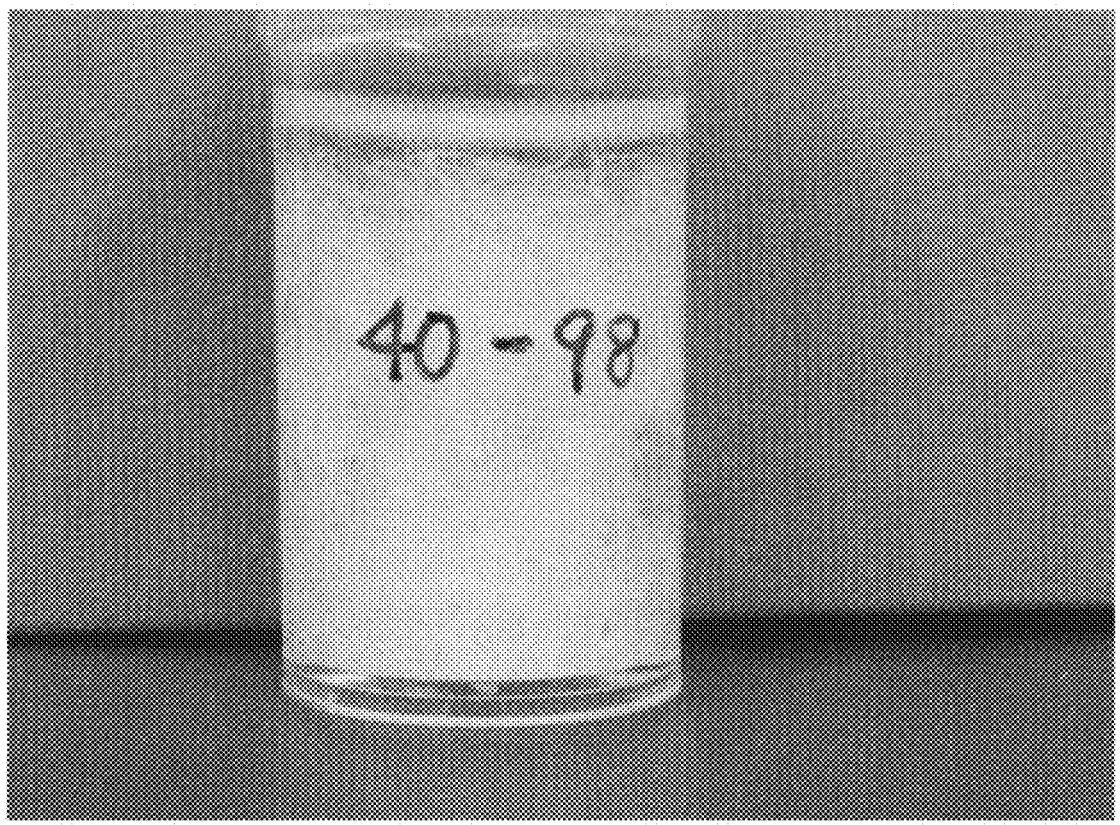
FIG. 2 is a photograph showing the fibers of the composite obtained with 100 mM $Ca(OH)_2$ in Example 1.

When the concentration of the calcium hydroxide suspension was 100 mM or lower, most of fibers were 3 mm or longer. In the case of 100 mM Ca(OH)₂, fibers were grown to a length of 5 mm and a thickness of about 100 μm on average, and sewing-thread-like fibers were formed (FIG. 2). The composite prepared with 100 mM Ca(OH)₂ had a high water content of 37% after dehydration pressing. In spite thereof, the strength of such composite was significantly enhanced (11.6±1.5 MPa) from that (9.8±0.3 MPa) of the composite prepared with 400 mM Ca(OH)₂ with a water content of 23%.

The swelling ratio had not varied 7 days later and thereafter (up until 21 days later). Empirically, the swelling ratio is preferably approximately 50% to 60% 7 days later, and all the test samples in this experiment were confirmed to be within this range.

5. Discussion

Actual ion concentrations in the reaction vessel can become different from the concentration in the reaction vessel determined above (supply of ion to the reaction vessel per minute (mM/min·ml)) with the elapse of time, based on the balance between the supply by feeding (including the increased amount of solution) and the consumption by composite formation. Under conditions where ideal composite formation takes place, supply evens out consumption, and this balance could be maintained at levels around the aforementioned concentration in the reaction vessel.

Under the conditions for this test, the average fiber lengths were uniformly 60 μm or longer in all examples. This indicates that a calcium ion concentration of 3.75 mM or lower and a phosphate ion concentration of 2.25 mM or lower in the reaction vessel can certainly yield an average fiber length exceeding 60 μm and a composite having an average fiber length of 1 mm or longer.

The aforementioned conditions could be set by adequately controlling the flow rate if the starting concentration of a calcium hydroxide suspension and that of an aqueous calcium phosphate solution were 400 mM or lower and 120 mM or lower, respectively.

Example 2

Examination of the Flow Rate

1. Testing Method

Subsequently, the influence of the flow rate upon self-organization of the composite was tested using calcium hydroxide suspensions of two different concentrations.

A) Low Concentration Calcium Hydroxide (100 mM)

An aqueous phosphoric acid solution (30 mM, 1,600 ml) comprising 800 ml of a 100-mM calcium hydroxide suspension and 2.01 g of pepsin-treated atelocollagen (extracted from porcine dermis, Nitta Gelatin Inc.) was used as a starting material. Pure water (800 ml) was previously placed in the reaction vessel, the flow rates were varied between 8 ml/min and 120 ml/min, and the composite was prepared in the same method as in Example 1. Under the above-described conditions, the ratio of the weight of hydroxyapatite (HAp) to that of collagen (Col) becomes 80:20 when an ideal reaction takes place.

B) High Concentration Calcium Phosphate (400 mM)

An experiment that was similar to the one in A) was carried out using, as starting materials, 200 ml of 400 mM-calcium hydroxide suspension and 400 ml of aqueous 120-mM phosphoric acid solution.

2. Evaluation of Composites

The obtained composites were subjected to measurement of fiber length, a three-point bending test, thermal analysis, and a swelling test in the same method as in Example 1. Results are shown in Table 2 (100 mM $Ca(OH)_2$) and Table 3 (400 mM $Ca(OH)_2$).

TABLE 2

Evaluation of properties of composites depending on flow rate (100 mM $Ca(OH)_2$)

|  |  | No. | | | | |
| --- | --- | --- | --- | --- | --- | --- |
|  |  | 6 | 7 | 8 | 9 | 10 |
| Flow rate of a calcium hydroxide solution (ml/min) | | 8 | 15 | 20 | 50 | 100 |
| Concentration of calcium hydroxide (mM) | | 100 | 100 | 100 | 100 | 100 |
| Amount of calcium hydroxide (ml) | | 800 | 800 | 800 | 800 | 800 |
| Concentration of an aqueous phosphoric acid solution (mM) | | 30 | 30 | 30 | 30 | 30 |
| Amount of an aqueous phosphoric acid solution (ml) | | 1,600 | 1,600 | 1,600 | 1,600 | 1,600 |
| Amount of pure water in a reaction vessel (ml) | | 800 | 800 | 800 | 800 | 800 |
| Ca concentration in a reaction vessel (mM) | | 0.5 | 0.94 | 1.25 | 3.13 | 6.25 |
| $PO_4$ concentration in a reaction vessel (mM) | | 0.3 | 0.56 | 0.75 | 1.88 | 3.75 |
| Fiber length - average | | 3–5 mm | 5–7 mm | 1–2 mm | 60 μm | 10 μm |
| Strength test | Strength (MPa) | 4.4 ± 0.5 | 20 ± 1 | 7.2 ± 0.8 | 5 ± 0.1 | 6 ± 0.3 |
|  | Young's modulus (GPa) | 0.20 ± 0.02 | 1.0 ± 0.1 | 0.32 ± 0.08 | 0.23 ± 0.10 | 0.18 ± 0.06 |
| Thermal analysis | Water content in the composite (%) | 55 | 37 | 35 | 22 | 20 |
|  | Amount of HAp in the composite (%) | 34 | 49 | 51 | 62 | 65 |
|  | Amount of Col in the composite (%) | 11 | 14 | 14 | 16 | 15 |
|  | HAp/Col ratio after dehydration | 76/24 | 78/22 | 78/22 | 79/21 | 81/19 |
| Swelling test | Swelling ratio 1 week later (%) | 28.2 | 32.3 | 36.8 | 52.2 | 51.8 |

TABLE 3

Evaluation of properties of composites depending on flow rate (400 mM $Ca(OH)_2$)

|  | No. | | | | |
| --- | --- | --- | --- | --- | --- |
|  | 11 | 12 | 13 | 14 | 15 |
| Flow rate (ml/min) | 8 | 10 | 15 | 20 | 50 |
| Concentration of calcium hydroxide (mM) | 400 | 400 | 400 | 400 | 400 |
| Amount of calcium hydroxide (ml) | 200 | 200 | 200 | 200 | 200 |

TABLE 3-continued

Evaluation of properties of composites depending on flow rate (400 mM Ca(OH)$_2$)

| | | No. | | | | |
|---|---|---|---|---|---|---|
| | | 11 | 12 | 13 | 14 | 15 |
| Concentration of an aqueous phosphoric acid solution (mM) | | 120 | 120 | 120 | 120 | 120 |
| Amount of an aqueous phosphoric acid solution (ml) | | 400 | 400 | 400 | 400 | 400 |
| Amount of pure water in a reaction vessel (ml) | | 200 | 200 | 200 | 200 | 200 |
| Ca concentration in a reaction vessel (mM) | | 8 | 10 | 15 | 20 | 50 |
| PO$_4$ concentration in a reaction vessel (mM) | | 4.8 | 6 | 9 | 12 | 30 |
| Fiber length - average | | 77 μm | 56 μm | 57 μm | 58 μm | 37 μm |
| Strength test | Strength (MPa) | 4.4 ± 0.5 | Unmeasurable | 20 ± 1 | 7.2 ± 0.8 | 5 ± 0.1 |
| | Young's modulus (GPa) | 0.20 ± 0.02 | Unmeasurable | 1.0 ± 0.1 | 0.32 ± 0.08 | 0.23 ± 0.10 |
| Thermal analysis | Water content in the composite (%) | 46 | 37 | 33 | 40 | 39 |
| | Amount of HAp in the composite (%) | 44 | 53 | 55 | 50 | 49 |
| | Amount of Col in the composite (%) | 10 | 10 | 12 | 10 | 12 |
| | HAp/Col ratio after dehydration | 81/19 | 84/16 | 82/18 | 83/14 | 80/20 |
| Swelling test | Swelling ratio 1 week later (%) | 33.8 | 38.5 | 48 | 22.8 | 47.2 |

Ion concentrations in the reaction vessel were determined by the same equation as that in Example 1. In this example wherein each reaction solution is excessively supplied, the actual ion concentrations in the reaction vessel can become higher than the values shown in these tables with the elapse of time.

3. Results

In the case of 100 mM Ca(OH)$_2$, composites having an average fiber length of 60 μm or longer were obtained when the flow rate of calcium hydroxide via a pump was 50 ml/min or lower (with an average flow rate of 25 ml/min). The maximal fiber length was obtained at a flow rate of 15 ml/min (5-7 mm). The fibers thereafter became shorter as the flow rate increased and their strength also decreased. When the flow rate exceeded a given level, calcium or phosphate ion supply exceeded the flow rate of composite formation. This increased the ion concentration in the reaction vessel with the elapse of time and blocked self-organization of the composites.

In the case of 400 mM Ca(OH)$_2$, composites having an average fiber length of 60 μm or longer were obtained only when the flow rate of calcium hydroxide via a pump was 8 ml/min or lower (with an average flow rate of 4 ml/min). When the flow rate exceeded the aforementioned level, the fibers became shorter as the flow rate increased, and their strength also decreased. A low collagen content in the composite and reduced self-organization show the possibility of dissolution of collagen in the reaction vessel.

4. Discussion

Results attained by this test revealed that a composite maintaining optimal concentrations of calcium and phosphate ions in the reaction vessel and having an excellent capacity for self-organization could be obtained by regulating the flow rate, provided that the starting concentration of calcium hydroxide was within a given range. It was also found that self-organization was difficult without considerable regulation of flow rates when the concentration of the calcium hydroxide or an aqueous phosphoric acid solution exceeded 400 mM and 120 mM, respectively.

Example 3

Preparation of Sheet-Like Organic/Inorganic Composite Biomaterials

Composites were prepared in the same method as in Example 1 using 800 ml of 100 mM calcium hydroxide suspension and 1,600 ml of aqueous 30 mM phosphoric acid solution (including 2.01 g of atelocollagen) at a flow rate for calcium hydroxide of 15 ml/min (with an average flow rate of 7.5 ml/min) in the presence of 800 ml of pure water in the reaction vessel. The resulting sediment was flattened and fixed in that state. Thus, the sheet-like organic/inorganic composite biomaterials were obtained.

Figure 3:
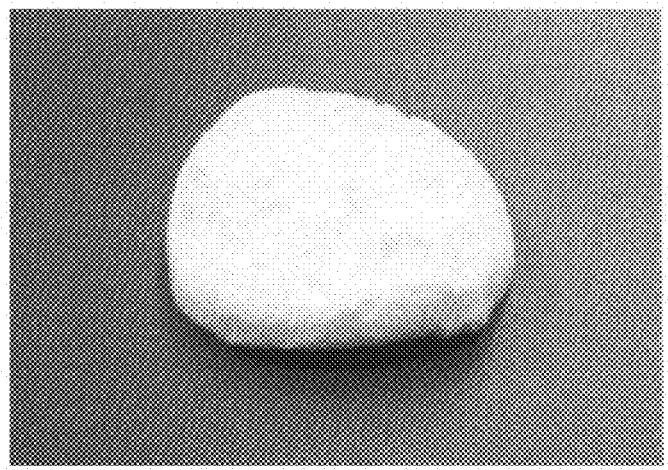
FIG. 3 is a photograph showing the organic/inorganic composite biomaterials of the present invention prepared in the form of porous bodies and sheets, wherein A represents a porous body, B represents a sheet (the entire backside), and C represents a sheet (an enlarged surface).
Figure 3:
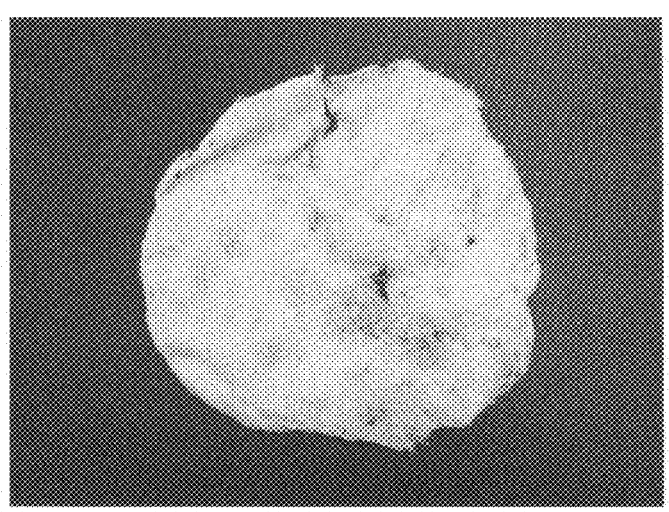
Figure 3:
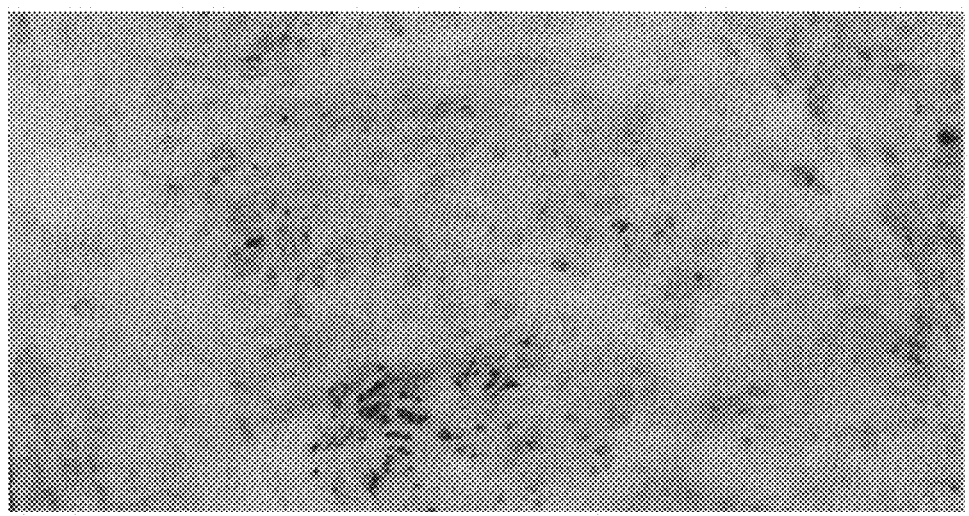

FIG. 3 is a photograph showing the obtained sheet-like solid substance (diameter: 14 cm; B represents the entire backside and C represents the enlarged surface) and a porous body solidified in a usual method (diameter: 25 mm; A).

The sheets were very strong, and the organic/inorganic composite biomaterials of the present invention having long fibers were considered to be suitable for the form of sheets.

Example 4

Preparation of Crosslinked Organic/Inorganic Composite Biomaterials

1. Crosslinking of an HAp/Col Composite

In accordance with the method described in Example 1, a calcium hydroxide suspension (40 mM, 2 dm$^3$) and an aqueous phosphoric acid solution (24 mM, 2 dm$^3$) containing collagen (2 g) were introduced into a reaction vessel via a tube pump to prepare an HAp/Col composite. The reaction solution was suspended and allowed to stand in that state for 3 hours. A crosslinking agent, glutaraldehyde, was added thereto while vigorously stirring, and the mixture was allowed to react for 10 minutes. After crosslinking, the composite was immediately filtered and washed three times with pure water. Crosslinking was carried out by varying the amount of glutaraldehyde within the range of 0.0191 to 13.5 mmol/g per g of collagen in the composite. With 0.191 mmol/g of glutaraldehyde, all the ε-amino groups in collagen molecules can be theoretically crosslinked thereto.

2. Assay of Property Values

Fibrous structures of the resulting crosslinked composites were observed using a Rapid-VueR transmission electron microscope (Beckman-Colter). The three-point bending strength and the swelling ratio were determined in the same method as in Example 1. Further, the amount of ε-amino groups was measured by the sulfo-SDTB analysis to determine the degree of crosslinking.

3. Results

1) As a result of observation under the transmission electron microscope, the average fiber length of a glutaraldehyde crosslinked composite was found to be 44.8 μm, and no macro-orientation was observed between the crosslinked hydroxyapatite and collagen. Thus, it was found that crosslinking randomly took place. A nanoscopic structure that was similar to that of natural bones (involving orientation of single collagen fiber HAp) was substantially maintained.

Figure 4:
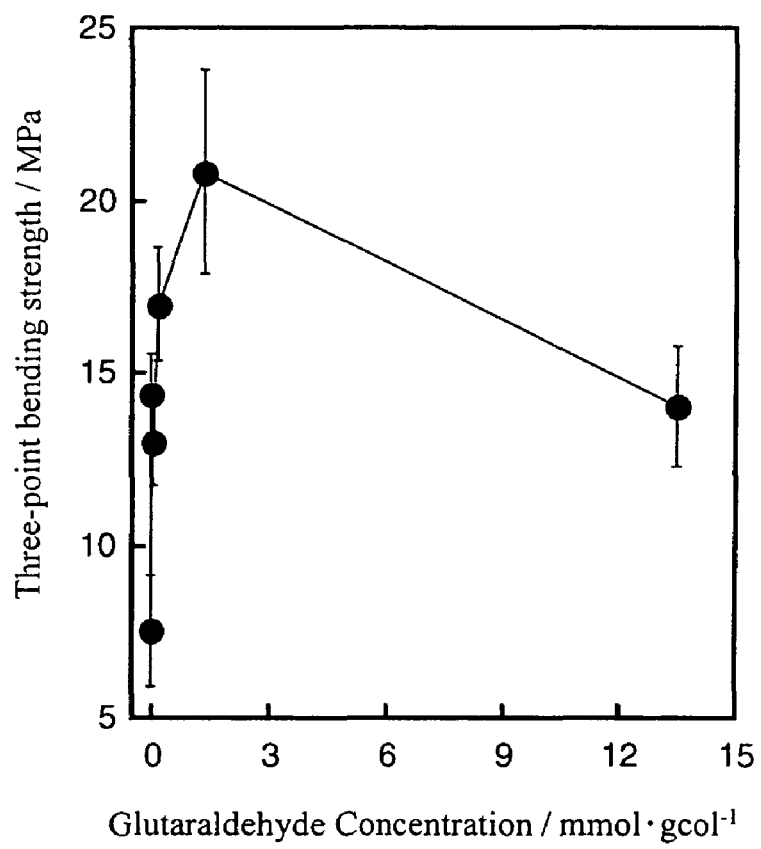
FIG. 4 shows the correlation between the degree of crosslinking and the three-point bending strength in the organic/inorganic composite biomaterials crosslinked with glutaraldehyde.
Figure 5:
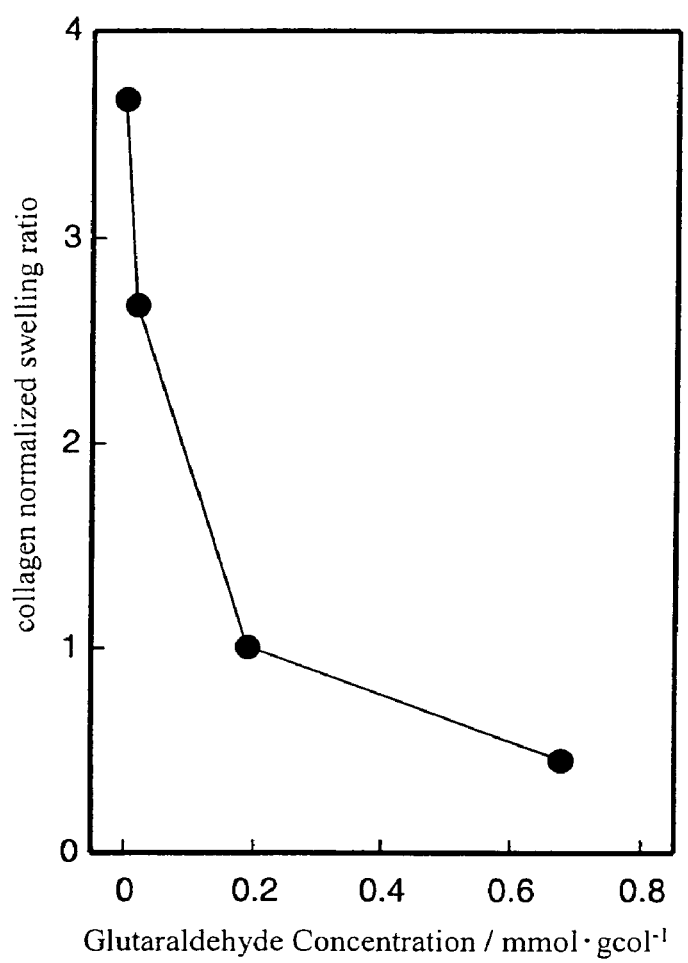
FIG. 5 shows the correlation between the degree of crosslinking and the swelling ratio in the organic/inorganic composite biomaterials crosslinked with glutaraldehyde.

2) The three-point bending strength was enhanced as the glutaraldehyde content increased, and it reached a maximal value at 1.35 mmol/g of collagen (FIG. 4). This indicates that an excess amount of glutaraldehyde crosslinking agent (1.35 mmol/g or more) introduces crosslinking between fibers constituting the composite and increases the water content therein, which disadvantageously inhibits a particle-particle bond and decreases the strength of the composite.

3) Since the swelling ratio depends on the amount of collagen, collagen normalized swelling ratio that reflected the degree of crosslinking was determined (FIG. 4). As a result, the swelling ratio was found to decrease depending on the concentration of glutaraldehyde, and biodegradability of the composite in body tissues could be regulated by crosslinking.

4) Results of sulfo-SDTB analysis demonstrated that no free ε-amino group was detected at a glutaraldehyde concentration of 1.35 mmol/g. This concentration is approximately 70 times higher than the amount of glutaraldehyde required for crosslinking crosslinkable functional groups in collagen.

4. Results

Glutaraldehyde was suitably added in an amount of 10 mmol or lower per g of collagen in order to maintain suitable mechanical strength for artificial bones. If the rate of biodegradation is proportional to the swelling ratio, a higher degree of crosslinking can result in more efficient inhibition of degradation. Nanoscopic structures (involving the orientation of single collagen fiber HAp) similar to those of natural bones were substantially maintained even after crosslinking.

Example 5

Test for Biodegradability of Crosslinked Organic/Inorganic Composite Biomaterials 1. Testing Method The biodegradability of the crosslinked HAp/Col composites was inspected by implanting the glutaraldehyde-crosslinked composites obtained in Example 4 (2×2×2 mm) in a rabbit tibia. These crosslinked composites were evaluated by visual inspection and histological examination (hematoxylin-eosin staining) 1, 2, and 4 weeks after implantation.

2. Results

The results of histological examination demonstrated that no toxic reaction, such as inflammatory reaction, was caused by the glutaraldehyde-crosslinked composites. Bone formation and bone conductivity equivalent to those in the case of non-crosslinked composites were observed in the vicinities of all the crosslinked composites.

The resorption/degradation rate of the crosslinked composites was reduced as the concentration of glutaraldehyde increased. In the case of the composite with high-degree of crosslinking (191 μmol or more), 70% to 80% of the composites still remained in bones even 4 weeks later. Specifically, approximately 50% of the composites crosslinked with 19.1 μmol of glutaraldehyde per g of collagen remained, and approximately 85% of the composites crosslinked with 675 μmol of glutaraldehyde per g of collagen remained. Further, only the surfaces of the composites crosslinked with 1.35 mmol of glutaraldehyde per g of collagen were resorbed, and 95% or more of the composites still remained. The amounts of remaining ε-amino groups were 80% to 95%, 0% to 10%, and 0% in each of the crosslinked samples. In particular, when the composite was crosslinked with 1.35 mmol of glutaraldehyde, an excess amount of glutaraldehyde formed a crosslinking network in the composites and further inhibited resorption of the composites.

3. Conclusion

Accordingly, composites crosslinked with 19.1 μmol to 1.35 mmol of glutaraldehyde per g of collagen were found to have the biodegradation rate required for artificial bones. Based on the above results and the results obtained in Example 4, mechanical strength and the biodegradation rate required for artificial bones can be realized if the composites of hydroxyapatite and collagen are crosslinked with at least approximately 10 μmol to 10 mmol of glutaraldehyde per g of collagen.

All publications, patents, and patent applications cited herein are incorporated herein by reference in their entirety.

INDUSTRIAL APPLICABILITY

The present invention provides organic/inorganic composite biomaterials having an average fiber length of 60 μm or longer and an excellent capacity for self-organization. These biomaterials have long fibers and enhanced strength and can be used in the form of sheets, porous bodies, or sponges in which fibers are interwined with each other. Also, the introduction of crosslinking in the biomaterials can provide a biodegradation rate suitable for artificial bones while maintaining the mechanical strength thereof.

The invention claimed is:

1. Organic/inorganic composite biomaterials, comprising: composites of hydroxyapatite and solubilized collagen, wherein said composites are constituted of fibers having an average fiber length of 60 μm or longer, and wherein the composites have microporous structures in which the c-axis of hydroxyapatite is oriented along collagen fibers.

2. The organic/inorganic composite biomaterials according to claim 1, wherein the solubilized collagen is an enzyme-solubilized collagen.

3. A process for producing the organic/inorganic composite biomaterials comprising composites of hydroxyapatite and collagen which are constituted of fibers having an average fiber length of 60 μm or longer, said composite having microporous structures in which the c-axis of hydroxyapatite is oriented along collagen fibers, said process comprising:
simultaneously adding to a reaction vessel an aqueous calcium salt solution and an aqueous phosphate solution containing collagen to maintain the calcium ion concentration at 3.75 mM or lower and the phosphate ion concentration at 2.25 mM or lower in the reaction vessel, and pressing the resulting composite, wherein the flow rates of the aqueous calcium salt solution and the aqueous phosphate solution being added to the reaction vessel are regulated such that the pH level of the reaction solution in the reaction vessel is maintained between 7 and 11, the average flow rate of the aqueous calcium salt solution being added to the reaction vessel being 5 to 25 ml/min; and wherein the starting concentration of the aqueous calcium salt solution is 50 to 200 mM, and the starting concentration of the aqueous phosphate solution is 15 to 96 mM.

4. The process according to claim 3, wherein the ratio of the weight of hydroxyapatite to that of collagen generated in the reaction vessel is between 3:2 and 9:1.

5. The process according to claim 3, wherein the ratio of the weight of hydroxyapatite to that of collagen generated is maintained between 70:30 and 85:15.

6. The process according to claim 3, wherein the temperature of the reaction solution is maintained between 35° C. and 40° C.

7. The process according to claim 3, further comprising introducing crosslinking of collagen in the organic/inorganic composite biomaterials obtained by the aforementioned process.

8. The process according to claim 7, wherein the crosslinking is introduced by a reaction utilizing glutaraldehyde.

9. The process according to claim 8, wherein 10 μmol to 10 mmol of the glutaraldehyde is used per g of collagen in organic/inorganic composite biomaterials.

10. The organic/inorganic composite biomaterials according to claim 1, wherein solubilized collagen is crosslinked.

11. The organic/inorganic composite biomaterials according to claim 1, which are formed into sheets, sponges, or porous bodies.

12. The process according to claim 3, wherein said calcium ion concentration is maintained at 2.5 mM or lower and said phosphate ion concentration is maintained at 1.5 mM or lower in the reaction vessel.

13. The organic/inorganic composite biomaterials according to claim 1, wherein said composites are constituted of fibers having an average fiber length of 1 mm or longer.

14. The organic/inorganic composite biomaterials according to claim 1, wherein said composites are constituted of fibers having an average fiber length of 3 mm or longer.

15. The organic/inorganic composite biomaterials according to claim 1, wherein said organic/inorganic composite biomaterials are produced by simultaneously adding to a reaction vessel an aqueous calcium salt solution and an aqueous phosphate solution containing solubilized collagen to maintain the calcium ion concentration at 3.75 mM or lower and the phosphate ion concentration at 2.25 mM or lower in the reaction vessel, and pressing the resulting composite, and wherein the starting concentration of the aqueous calcium salt solution is 50 to 200 mM, and the starting concentration of the aqueous phosphate solution is 15 to 96 mM.

16. The process according to claim 3, wherein the pH level of the reaction solution in the reaction vessel is maintained between 7 and 9.

17. The process according to claim 3, wherein the pH level of the reaction solution in the reaction vessel is maintained at pH 9±0.3.

18. The process according to claim 17, wherein the temperature of the reaction solution is maintained at 40° C.

19. The process according to claim 6, wherein the temperature of the reaction solution is maintained at 40° C.

* * * * *

UNITED STATES PATENT AND TRADEMARK OFFICE
CERTIFICATE OF CORRECTION

PATENT NO. : 8,168,151 B2
APPLICATION NO. : 10/492937
DATED : May 1, 2012
INVENTOR(S) : Junzo Tanaka et al.

It is certified that error appears in the above-identified patent and that said Letters Patent is hereby corrected as shown below:

On the Title page, Item (73):
Change

"(73) Assignee: Japan Science and Technology Agency, Kawaguchi-shi, Japan"

To be

--(73) Assignee: Japan Science and Technology Agency, Kawaguchi-shi, Japan
National Institute For Materials Science, Tsukuba-shi, Ibaraki, Japan
Nitta Gelatin Inc., Osaka-shi, Osaka, Japan--

Signed and Sealed this
Second Day of April, 2013

Teresa Stanek Rea
*Acting Director of the United States Patent and Trademark Office*